United States Patent [19]

Haugwitz et al.

[11] 4,006,137
[45] Feb. 1, 1977

[54] 2-ETHENYL IMIDAZOLIUM DERIVATIVES

[75] Inventors: Rudiger D. Haugwitz; Barbara V. Maurer, both of Titusville, N.J.

[73] Assignee: E. R. Squibb & Sons, Inc., Princeton, N.J.

[22] Filed: Aug. 21, 1975

[21] Appl. No.: 606,387

[52] U.S. Cl. .................. 260/240 D; 260/240 A; 260/240 E; 260/240 R; 260/240.9
[51] Int. Cl.² ............. C07D 233/06; C07D 403/06
[58] Field of Search ........ 260/240 E, 240 D, 240.9, 260/240 R, 240 A

[56] References Cited

UNITED STATES PATENTS

| | | | |
|---|---|---|---|
| 3,502,661 | 3/1970 | Kasubick et al. | 260/240 E |
| 3,549,626 | 12/1970 | Miller | 260/240 E |
| 3,592,653 | 7/1971 | Fumia et al. | 260/240 E |
| 3,658,797 | 4/1972 | Ross et al. | 260/240 E |
| 3,684,802 | 8/1972 | McFarland | 260/240 E |

FOREIGN PATENTS OR APPLICATIONS

| | | | |
|---|---|---|---|
| 1,501,756 | 10/1967 | France | 260/240 E |

OTHER PUBLICATIONS

McFarland et al., (II), J. Med. Chem., 12 (1969), p. 1079.

*Primary Examiner*—Arthur P. Demers
*Attorney, Agent, or Firm*—Lawrence S. Levinson; Merle J. Smith; Donald J. Barrack

[57] ABSTRACT

Compounds having the structure

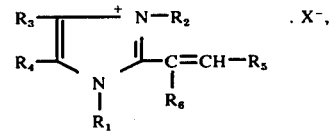

wherein $R_1$ and $R_2$ are the same or different and are alkyl, benzyl, or allyl; $R_3$ and $R_4$ are the same or different and are hydrogen, alkyl, phenyl, or halogen; $R_5$ is phenyl, naphthalenyl, 1,3-benzodioxolyl, pyridinyl, thienyl, furyl, pyrrolyl, quinolinyl, benzimidazolyl or a quaternary ammonium salt of pyridinyl, quinolinyl or benzimidazolyl; $R_6$ is hydrogen, methyl or phenyl; and X is chlorine, bromine, or iodine have useful anthelmintic properties.

8 Claims, No Drawings

2-ETHENYL IMIDAZOLIUM DERIVATIVES

SUMMARY OF THE INVENTION

Nematocidal activity is exhibited by compounds having the formula

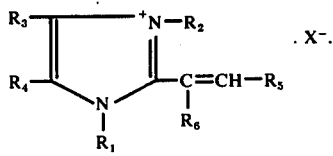

In formula I, and throughout the specification, the symbols are as defined below.

$R_1$ and $R_2$ can be the same or different and can be alkyl, benzyl, or allyl;

$R_3$ and $R_4$ can be the same or different and can be hydrogen, alkyl, phenyl, or halogen;

$R_5$ can be phenyl, naphthalenyl, 1,3-benzodioxolyl, pyridinyl, thienyl, furyl, pyrrolyl, quinolinyl, benzimidazolyl, or a quaternary ammonium salt of pyridinyl, quinolinyl, or benzimidazolyl, or any one of the above groups substituted with one or two halogen, nitro, dialkylamino, trifluoromethyl, alkyl, or alkoxy groups; the $R_5$ group is connected to the ethenyl group through an available carbon atom;

$R_6$ can be hydrogen, methyl or phenyl; and

X can be chlorine, bromine or iodine.

The terms "alkyl" and "alkoxy", as used throughout the specification, refer to groups having 1 to 3 carbon atoms; methyl and methoxy are preferred.

DETAILED DESCRIPTION OF THE INVENTION

The imidazolium derivatives of formula I can be prepared by reacting a compound having the formula

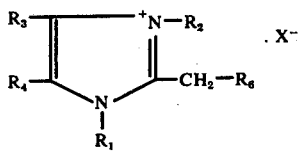

with an aldehyde having the formula

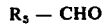

in the presence of a strong base, e.g., an alkali metal alkoxide or an alkali metal hydroxide, such as sodium methoxide or sodium hydroxide. The reaction is run in an organic solvent, e.g., a lower alkanol such as methanol or ethanol, or in an ether such as glyme. Reaction conditions are not critical and the reaction can be conveniently run at room temperature or at slightly elevated temperatures.

Those compounds of formula I wherein $R_5$ is a quaternary ammonium salt of pyridinyl, quinolinyl, or benzimidazolyl can preferably be prepared from the compounds of formula I wherein $R_5$ is the corresponding non-quaternized heterocyclic group using procedures well known in the art. The compounds of formula I wherein $R_5$ is pyridinyl, quinolinyl, or benzimidazolyl form quaternary ammonium salts with alkyl halides (e.g., methyl iodide), benzyl halides (e.g., benzyl bromide), and dialkyl sulfates (e.g., dimethyl sulfate).

The starting materials of formula II are readily obtainable, using procedures well known in the art, by quaternization of imidazoles having the formula

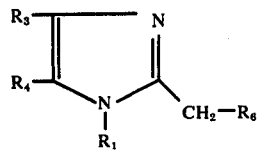

The 2-ethenyl imidazolium derivatives of this invention have useful nematocidal activity and can be used to treat nematode infections in domestic and farm animals such as dogs, cats, swine, horses, cattle, sheep and goats. The effective dose level for the treatment of nematode infections with the compounds of this invention ranges from about 50 to about 300 milligrams of active ingredient per kilogram of animal body weight per day. The optimal dosage will usually be in the range of from about 100 to about 200 milligrams of active ingredient per kilogram of animal body weight per day. The compounds of this invention can be administered orally or by injection. It is preferred that they be administered orally as part of the subject animal's feed or in its drinking water.

The following examples are specific embodiments of this invention.

EXAMPLE 1

2-[2-(4-Methoxyphenyl)etheryl]-1,3-dimethyl-1H-imidazolium iodide

A. 1,2,3-Trimethyl-1H-imidazolium iodide

To 20 g of 1,2-dimethylimidazole dissolved in 100 ml of ether there is added 20 ml of methyl iodide. On standing the product precipitates and is filtered off. Two crystallizations from ethanol-ether furnish the pure product, melting point 315°–318° C.

B. 2-[2-(4-Methoxyphenyl)ethenyl]-1,3-dimethyl-1H-imidazolium iodide

A mixture of 10 g of 1,2,3-trimethyl-1H-imidazolium iodide, 2.0 g of potassium hydroxide and 10 ml of 4-methoxybenzaldehyde is refluxed in 50 ml of absolute ethanol for 15 minutes during which time a precipitate is formed. The reaction mixture is cooled and the solid is filtered off. Crystallization from absolute ethanol yields 9.1 g of the title compound, melting point 289°–291° C.

EXAMPLE 2

1,3-Dimethyl-2-[2-(2-pyridinyl)ethenyl]-1H-imidazolium iodide

A mixture of 12.0 g of 1,2,3-trimethyl-1H-imidazolium iodide and 12 ml of 2-pyridinecarboxaldehyde in 40 ml of 10% potassium hydroxide in absolute ethanol is refluxed for 15 minutes. The resulting solid is filtered off and crystallized from absolute ethanol to yield 3.5 g of the title compound, melting point 306° C.

EXAMPLE 3

1,3-Dimethyl-2-[2-(1-methyl-1H-pyrrol-2-yl)ethenyl]-1H-imidazolium iodide

A mixture of 12.0 g of 1,2,3-trimethyl-1H-imidazolium iodide, 2g of potassium hydroxide and 12.0 g of N-methylpyrrole-2-carboxaldehyde in 60 ml of absolute ethanol is refluxed for 15 minutes during which time a precipitate is formed. The mixture is cooled and 10 ml of water is added. The solid is filtered off and crystallized from absolute ethanol to yield 12.3 g of the title compound, melting point 289°–291° C.

EXAMPLE 4

1,3-Dimethyl-2-[2-(2-furanyl)ethenyl]-1H-imidazolium iodide

A mixture of 5.0 g of 1,2,3-trimethyl-1H-imidazolium iodide, 2.5 ml of furfural, 20 ml of ethanol and 1 g of potassium hydroxide is refluxed for 10 minutes. The mixture is cooled, water is added, and the resulting solid is filtered off and crystallized from ethanol to yield 5.0 g of the title compound, melting point 299°–300° C.

EXAMPLE 5

2-[2-(4-Chlorophenyl)ethenyl]-1,3-dimethyl-1H-imidazolium iodide

A mixture of 6.0 g of 1,2,3-trimethyl-1H-imidazolium iodide, 1g of potassium hydroxide, and 6 g of p-chlorobenzaldehyde is refluxed in 25 ml of absolute ethanol for 15 minutes during which time a precipitate is formed. The reaction mixture is cooled, 5 ml of water is added, and the solid is filtered off and dried. Crystallization from absolute ethanol yields 5.4 g of the title compound, melting point 266°–268° C.

EXAMPLE 6

1,3-Dimethyl-2-[2-(2-thienyl)ethenyl]-1H-imidazolium iodide

A mixture of 5.0 g of 1,2,3-trimethyl-1H-imidazolium iodide, 2ml of 2-thiophenecarboxaldehyde, 20 ml of absolute ethanol and 1 g of potassium hydroxide is refluxed for 25 minutes. Water is added to the cooled mixture and the resulting solid is filtered off. Recrystallization from ethanol yields 3.8 g of the title compound, melting point 309°–311° C.

EXAMPLE 7

1,3-Dimethyl-2-[2-(1-naphthalenyl)ethenyl]-1H-imidazolium iodide

A mixture of 6.0 g of 1,2,3-trimethyl-1H-imidazolium iodide, 1 g of potassium hydroxide and 6 ml of 1-naphthaldehyde in 25 ml of methanol is refluxed for 15 minutes during which time a precipitate is formed. The reaction mixture is cooled and 5 ml of water is added. The solid is filtered off, dried, and crystallized from absolute ethanol to yield 3.7 g of the title compound, melting point 251°–253° C.

EXAMPLES 8–17

Following the procedure of Example 1, but substituting the compound listed in column I for 1,2-dimethylimidazole, the compound listed in column II for methyl iodide, and the compound listed in column III for 4-methoxybenzaldehyde, yields the compound listed in column IV.

| | Column I | Column II | Column III | Column IV |
|---|---|---|---|---|
| 8 | 1-benzyl-2-methylimidazole | benzyl chloride | benzaldehyde | 1,3-dibenzyl-2-(2-phenylethenyl)-1H-imidazolium chloride |
| 9 | 1-allyl-2-methylimidazole | allyl bromide | 1-naphthaldehyde | 1,3-diallyl-2-(2-naphthylethenyl)-1H-imidazolium bromide |
| 10 | 1-ethyl-2-methylimidazole | ethyl iodide | 2-pyridinecarboxaldehyde | 1,3-diethyl-2-(2-pyridinylethenyl)-1H-imidazolium iodide |
| 11 | 2-ethyl-1-methylimidazole | methyl iodide | piperonal | 2-[2-(1,3-benzodioxol-5-yl)-1-methylethenyl]-1,3-dimethyl-1H-imidazolium iodide |
| 12 | 2-benzyl-1-methylimidazole | methyl iodide | 4-quinolinecarboxaldehyde | 1,3-dimethyl-2-(1-phenyl-2-quinolin-4-yl-ethenyl)-1H-imidazolium iodide |
| 13 | 1,2-dibenzylimidazole | benzyl iodide | 2-benzimidazolecarboxaldehyde | 1,3-dibenzyl-2-(2-benzimidazol-2-yl-1-phenylethenyl)-1H-imidazolium iodide |
| 14 | 4,5-dichloro-1,2-dimethylimidazole | methyl iodide | 2-chlorobenzaldehyde | 4,5-dichloro-2-[2-(2-chlorophenyl)-ethenyl]-1,3-dimethyl-1H-imidazolium iodide |
| 15 | 1,2-dimethyl-4-phenylimidazole | methyl iodide | 3-(trifluoromethyl)benzaldehyde | 1,3-dimethyl-4-phenyl-2-[2-[3-(trifluoromethyl)phenyl]ethenyl]-1H-imidazolium iodide |
| 16 | 1,2,4,5-tetramethylimidazole | methyl iodide | 4-(dimethylamino)benzaldehyde | 2-[2-[4-(dimethylamino)phenyl]ethenyl]-1,3,4,5-tetramethyl-1H-imidazolium iodide |
| 17 | 1,2-dimethylimidazole | methyl iodide | 4-nitrobenzaldehyde | 1,3-dimethyl-2-[2-(4-nitrophenyl)-ethenyl]-1H-imidazolium iodide |

EXAMPLE 18

2-[2-(1,3-Dimethyl-1H-imidazolium-2-yl)ethenyl]-1-methylpyridinium iodide (1:2)

1,3-Dimethyl-2-[2-(2-pyridinyl)ethenyl]-1H-imidazolium iodide (6.5 g) and 10 ml of methyl iodide are refluxed in 20 ml of acetonitrile for one hour. The resulting solid is filtered off and crystallized from methanol to yield 5.5 g of the title compound, melting point 75° C.

What is claimed is:
1. A compound selected from the group consisting of 2-[2-(4-methoxyphenyl)ethenyl]-1,3-dimethyl-1H-imidazolium iodide; 1,3-dimethyl-2-[2-(2-pyridinyl)ethenyl]-1H-imidazolium iodide; 1,3-dimethyl-2-[2-(1-methyl-1H-pyrrol-2-yl)ethenyl]-1H-imidazolium iodide; 1,3-dimethyl-2-[2-(2-furanyl)ethenyl]-1H-imidazolium iodide; 2-[2-(4-chlorophenyl)ethenyl]-1,3-dimethyl-1H-imidazolium iodide; 1,3-dimethyl-2-[2-(2-thienyl)-ethenyl]-1H-imidazolium iodide; and 1,3-dimethyl-2-[2-(1-naphthalenyl)ethenyl]-1H-imidazolium iodide.

2. The compound in accordance with claim 1 having the name 2-[2-(4-methoxyphenyl)ethenyl]-1,3-dimethyl-1H-imidazolium iodide.

3. The compound in accordance with claim 1 having the name 1,3-dimethyl-2-[2-(2-pyridinyl)ethenyl]-1H-imidazolium iodide.

4. The compound in accordance with claim 1 having the name 1,3-dimethyl-2-[2-(1-methyl-1H-pyrrol-2-yl)ethenyl]-1H-imidazolium iodide.

5. The compound in accordance with claim 1 having the name 1,3-dimethyl-2-[2-(2-furanyl)ethenyl]-1H-imidazolium iodide.

6. The compound in accordance with claim 1 having the name 2-[2-(4-chlorophenyl)ethenyl]-1,3-dimethyl-1H-imidazolium iodide.

7. The compound in accordance with claim 1 having the name 1,3-dimethyl-2-[2-(2-thienyl)ethenyl]-1H-imidazolium iodide.

8. The compound in accordance with claim 1 having the name 1,3-dimethyl-2-[2-(1-naphthanlenyl)ethenyl]-1H-imidazolium iodide.

* * * * *